United States Patent
Ostrovsky et al.

(10) Patent No.: US 7,799,049 B2
(45) Date of Patent: Sep. 21, 2010

(54) ATRAUMATIC ANCHORING AND DISENGAGEMENT MECHANISM FOR PERMANENT IMPLANT DEVICE

(75) Inventors: Isaac Ostrovsky, Wellesley, MA (US); Michael J. Wallace, Bellaire, TX (US); Hannah Kim, Boxborough, MA (US); Peter Shank, Boylston, MA (US); Kristian DiMatteo, Maynard, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 444 days.

(21) Appl. No.: 10/155,367

(22) Filed: May 23, 2002

(65) Prior Publication Data

US 2002/0138097 A1 Sep. 26, 2002

Related U.S. Application Data

(63) Continuation of application No. 08/978,403, filed on Nov. 25, 1997, now Pat. No. 6,447,530, which is a continuation-in-part of application No. 08/942,531, filed on Oct. 2, 1997, now abandoned, which is a continuation-in-part of application No. 08/757,827, filed on Nov. 27, 1996, now abandoned.

(51) Int. Cl.
A61M 29/00 (2006.01)
(52) U.S. Cl. .................................................. 606/200
(58) Field of Classification Search .............. 606/200, 606/191, 198, 199, 108, 127, 159
See application file for complete search history.

(56) References Cited

U.S. PATENT DOCUMENTS 4,425,908 A * 1/1984 Simon .................... 128/899

(Continued)

FOREIGN PATENT DOCUMENTS

EP 0 678 284 A1 10/1995

(Continued)

*Primary Examiner*—Anhtuan T Nguyen
*Assistant Examiner*—Tuan V Nguyen
(74) *Attorney, Agent, or Firm*—Crompton, Seager & Tufte LLC (57) ABSTRACT

A recoverable thrombosis filter that may be recoverable by a single recovery procedure. It can include a plurality of thrombosis filtering elements that are shaped in a predetermined manner and which are joined at one end and are deployed about a longitudinal axis to form a generally conical structure. The filtering elements can include shaped ends for engaging an inner lumen wall.

22 Claims, 12 Drawing Sheets

U.S. PATENT DOCUMENTS

| | | | |
|---|---|---|---|
| 4,688,553 A * | 8/1987 | Metais | 128/899 |
| 4,817,600 A * | 4/1989 | Herms et al. | 606/198 |
| 4,990,156 A * | 2/1991 | Lefebvre | 606/200 |
| 5,059,205 A * | 10/1991 | El-Nounou et al. | 606/200 |
| 5,133,733 A * | 7/1992 | Rasmussen et al. | 606/200 |
| 5,234,458 A * | 8/1993 | Metais | 606/200 |
| 5,242,462 A | 9/1993 | El-Nounou et al. | |
| 5,344,427 A * | 9/1994 | Cottenceau et al. | 606/200 |
| 5,370,657 A | 12/1994 | Irie | |
| 5,383,887 A | 1/1995 | Nadal | |
| 5,601,595 A * | 2/1997 | Smith | 606/200 |
| 5,634,942 A * | 6/1997 | Chevillon et al. | 623/1.1 |
| 5,669,933 A * | 9/1997 | Simon et al. | 600/200 |
| 5,776,162 A * | 7/1998 | Kleshinski | 623/1.18 |
| 5,836,968 A * | 11/1998 | Simon et al. | 606/200 |
| 5,836,969 A * | 11/1998 | Kim et al. | 606/200 |
| 5,853,420 A * | 12/1998 | Chevillon et al. | 606/200 |
| 5,976,172 A * | 11/1999 | Homsma et al. | 606/200 |
| 6,007,558 A * | 12/1999 | Ravenscroft et al. | 606/200 |
| 6,013,093 A * | 1/2000 | Nott et al. | 606/200 |
| 6,193,739 B1 | 2/2001 | Chevillon et al. | |
| 6,391,045 B1 * | 5/2002 | Kim et al. | 606/200 |
| 6,447,530 B1 * | 9/2002 | Ostrovsky et al. | 606/200 |
| 6,706,054 B2 * | 3/2004 | Wessman et al. | 606/200 |
| 6,872,217 B2 * | 3/2005 | Walak et al. | 606/200 |
| 2001/0011181 A1 * | 8/2001 | DiMatteo | 606/200 |

FOREIGN PATENT DOCUMENTS

| | | | | |
|---|---|---|---|---|
| FR | 2 718 950 | | 10/1995 | |
| WO | 93/12723 | * | 7/1993 | 606/200 |
| WO | WO 94/07431 | | 4/1994 | |
| WO | WO 95/09567 | | 4/1995 | |

* cited by examiner

ATRAUMATIC ANCHORING AND DISENGAGEMENT MECHANISM FOR PERMANENT IMPLANT DEVICE

CROSS REFERENCE TO RELATED APPLICATION

This is a continuation of application Ser. No. 08/978,403, filed on Nov. 25, 1997 now U.S. Pat. No. 6,447,530, which in turn is a continuation-in-part of application Ser. No. 08/942,531, filed Oct. 2, 1997 now abandoned, which in turn is a continuation-in-part of application Ser. No. 08/757,827, filed Nov. 27, 1996 now abandoned.

TECHNICAL FIELD

The present invention relates to improved thrombosis filters. More particularly, the invention relates to a thrombosis filter that can be percutaneously installed in a selected body lumen at a selected location in the vascular system and is adapted for trapping thrombosis materials or blood clots. Still more particularly, the invention relates to a thrombosis filter that can be percutaneously removed from the vascular system from a single direction.

BACKGROUND OF THE INVENTION

Pulmonary embolism is a recognized medical emergency, and may be caused by venous thrombosis. The venous thrombosis may be caused by blood flow retention, venous intima damage, or coagulation abnormalities. Recognized treatments include administration of anti-coagulant medication therapy, thrombolytic therapy, thrombectomy, and inferior vena cava thrombosis filtering procedures. When an inferior vena cava thrombosis filtering procedure is selected, it can be accomplished using either a laparotomy procedure under general anesthesia, or percutaneously inserting a thrombosis filter under local anesthetic. A laparotomy procedure is a surgical procedure done under general anesthesia, and is susceptible to thrombosis formation due to discontinuance of anti-coagulant therapy prior to such surgery.

A recognized option is to intravenously insert a thrombosis filter in the vascular system, and in particular into the inferior vena cava, which requires only a local anesthetic. Percutaneous filter insertion has been recognized as an effecateous procedure since only a local anesthetic is required; however, such thrombosis filters have been recognized to become affixed to the inner vena cava wall or vein wall by neointimal hyperplasia within a relatively short time after implantation. This process can occur within two or three weeks, and in prior art filter arrangements renders the filter unremovable by a single percutaneous process without incurring significant vessel trauma.

There are a number of thrombosis filters which have been developed with the intent of allowing percutaneous removal. Those prior art thrombosis filters that include substantially linear struts tend to distribute forces along the longitudinal axis of the struts. With the struts deployed outwardly to engage the walls of the lumen, asymmetrical compression of the lumen can cause the struts to be forced together in a manner that causes the struts to do damage to the lumen wall.

As indicated, there are a number of prior art implantable filters. One example is the filter disclosed in U.S. Pat. No. 4,817,600 issued to James Kay Herms, et al., which describes a set of shaped leg portions that are joined at one end and are arranged at an acute angle to the axis of the filter, and form a generally conical arrangement. The shaped legs include hooks at the extremity for hooking into the vein wall and holding the filter in position against the flow of blood within the lumen. Herms, et al. provided for an improved leg structure that would avoid some of the concerns of the filters that used relatively straight struts, and minimized the damage that could occur to the vessel or lumen arising from tipping or tilting of the filter. It did not, however, describe a structure or method for percutaneously removing the filter.

U.S. Pat. No. 4,990,156 to J. Lefebvre describes a filter that may be percutaneously inserted for temporary use in determining whether or not a more permanent filtering treatment is necessary. The device describes a non-aggressive contact of the filter elements with the vessel and describes a number of elements that each have sharpened and roughened portions contacting the vessel wall and holding the filter in position. A sheath is provided to allow removal should the filter not be required for permanent usage. Once deployed, the filter is positioned for definitive use and may not thereafter be readily removed.

U.S. Pat. No. 5,324,304 issued to Erik Rasmussen, describes another form of implantable filter that is self-expandable and can be inserted through use of a catheter which encloses the structure. The anchoring legs are designed to have hooks at the ends for engaging the wall of the vein once deployed. The anchoring elements form part of the filtering structure, and once placed would tend to hook firmly into the vein walls. No structure or method is described for percutaneous removal.

U.S. Pat. No. 5,370,657 to Toshiyuki Irie describes a recoverable thrombosis filter having a structure wherein the holding mechanism and the filtering mechanism is comprised of a number of opposed elements that are held in place by an intermediate tension member. It recognizes that removal may be desirable, and has described a series of shaped end portions that cooperate with the wall of the vessel, without piercing it deeply. For removal, it is necessary that dual percutaneous procedures be worked from opposite ends of the filter. A pair of hooking devices are engaged from the opposite ends, and the two halves of the filter are stretched apart until the connecting tension member breaks. While the two halves of the filter are drawn within a pair of sheaths for withdrawal, this removal procedure requires that two opposed removal structures be administered to the opposite ends of the filter, and that manipulation of the two removal devices be coordinated to grasp the opposed hooking elements such that the filter can be broken in half and withdrawn. This removal process doubles the risk to the patient, and due to the small size of the elements, is relatively difficult to accomplish.

The foregoing described prior art is illustrative of various types of filter structures and handling devices that are known for use in placing and removing thrombosis filters. The prior art structures do not describe filter structures that are readily removable utilizing a single percutaneous removal procedure.

To address the deficiencies in the prior art, the present invention was developed to provide an improved recoverable thrombosis filter that can be removed through a percutaneous procedure even after having been in place for such time as to have had neointimal hyperplasia to have fully developed. Through the use of a unique holding structure and a filtering portion of the thrombosis filter, the filter is structured such that the holding portion can be collapsed from one end through external manipulation and the entire filter drawn within an enclosing structure for removal. These and other more detailed specific objectives of the invention will become apparent to those skilled in the art from consideration of the drawings and the description of the preferred embodiments.

SUMMARY OF THE INVENTION

The present invention comprises a recoverable thrombosis filter that is recoverable by a single recovery procedure. It includes a plurality of thrombosis filtering elements that are shaped in a predetermined manner and which are joined at one end and are deployed about a longitudinal axis to form a generally conical structure. The filtering elements include shaped ends for engaging an inner lumen wall. A plurality of positioning struts are joined at one end and are deployed in an opposite direction around the longitudinal axis. The positioning struts include wall engaging ends that include projections for engaging the inner wall of the lumen to prevent motion of the filter structure in the direction of deployment of the positioning struts. The anchoring device of the present application can be used with other devices such as stents, stent grafts, vaso-occlusive particles, vascular closure devices, filters and the like.

A recovery mechanism including retracting structure is percutaneously inserted to the vicinity of the filter. The recovery mechanism includes an extensible gripping device, an actuating device, and an outer shield capable of enclosing the filter. The gripping device is manipulated to engage a portion of the retracting structure so that the filter can be held in position. The activating device of the recovery mechanism operates to collapse the plurality of positioning struts to a position where they can be withdrawn by the gripping device into the outer shield. While the outer shield is held firmly in position, the gripping device is further withdrawn and the plurality of thrombosis filtering structures are withdrawn into the shield.

In one embodiment of the removable structure for the thrombosis filter, a retracting mechanism, in combination with the recovery mechanism, causes the plurality of positioning struts to be withdrawn from contact with the inner lumen wall and to be deflected into a substantially parallel relationship with the struts arranged longitudinally in the direction of their original deployment.

In another embodiment, the recovery mechanism engages the removable thrombosis filter and holds it in place while the plurality of positioning struts are moved in the direction opposite of their original deployment and are forced into a generally parallel alignment along the longitudinal axis directed toward the direction of deployment of the filtering elements. Once deflected, the outer shield is held in place and the filter is drawn within the outer shield.

The present invention is thus an improved removable thrombosis filter and method for removal allowing percutaneous removal by a recovery mechanism engaging one end of the filter. Additional features of the invention and the advantages derived therefrom, and the various scopes and aspects of the invention will become apparent from the drawings, the description of the preferred embodiments of the invention, and the claims.

DETAILED DESCRIPTION OF THE PREFERRED EMBODIMENTS

Figure 1:
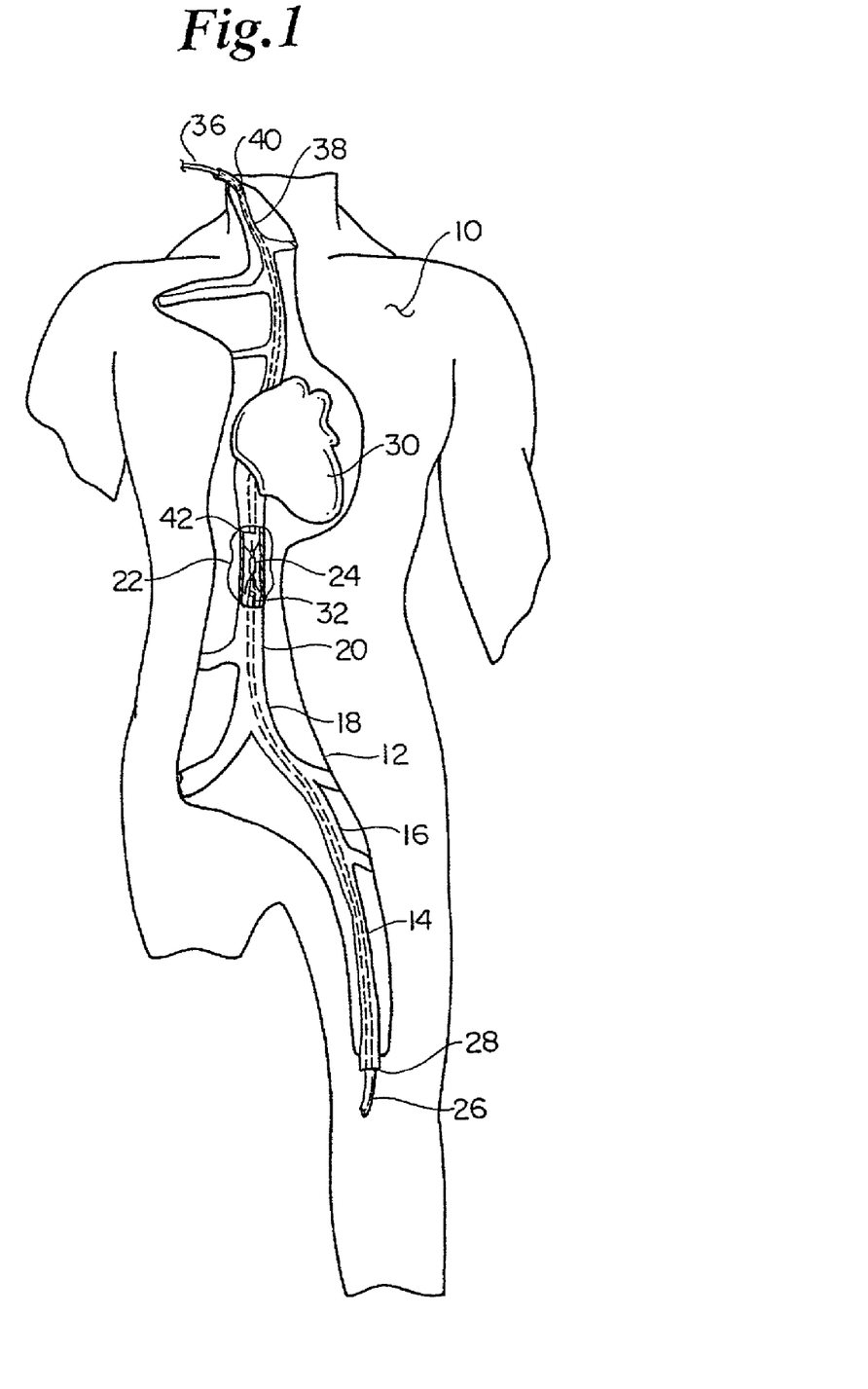
FIG. 1 is a fragmentary section through a human body from left to right and illustrates a medical procedure of installing the thrombosis filter in the inferior vena cava and removal of the filter by percutaneously entering the venous system at the jugular vein and withdrawing the filter.

FIG. 1 is a fragmentary section through a human body from left to right and illustrates a medical procedure of installing the thrombosis filter in the inferior vena cava and removal of the filter by percutaneously entering the venous system at the jugular vein and withdrawing the filter. This illustrates the body 10 with a cutaway portion 12 that exposes a portion of the vascular system. The femoral vein 14 leads to the external iliac vein 16. The common iliac vein 18 leads to the inferior vena cava 20. As illustrated at the cutaway section 22, a filter 24 is dispersed within the inferior vena cava and is held in place by the structure that will be described. As shown, a catheter tube is inserted at incision 28 into the venous system. As it extends toward heart 30, it reaches the inferior vena cava 20 and the filter 24 is deployed. The distal end 32 of the catheter structure 26 is shown after deployment of the filter 24. For withdrawal or removal of filter 24, a recovery mechanism (36) is inserted in the jugular vein 38 at incision 40 and passes through an atrium of heart 30 until its distal end 42 enters the inferior vena cava 20. The recovery mechanism is not shown in detail in this figure, but will be described in detail below.

Figure 2:
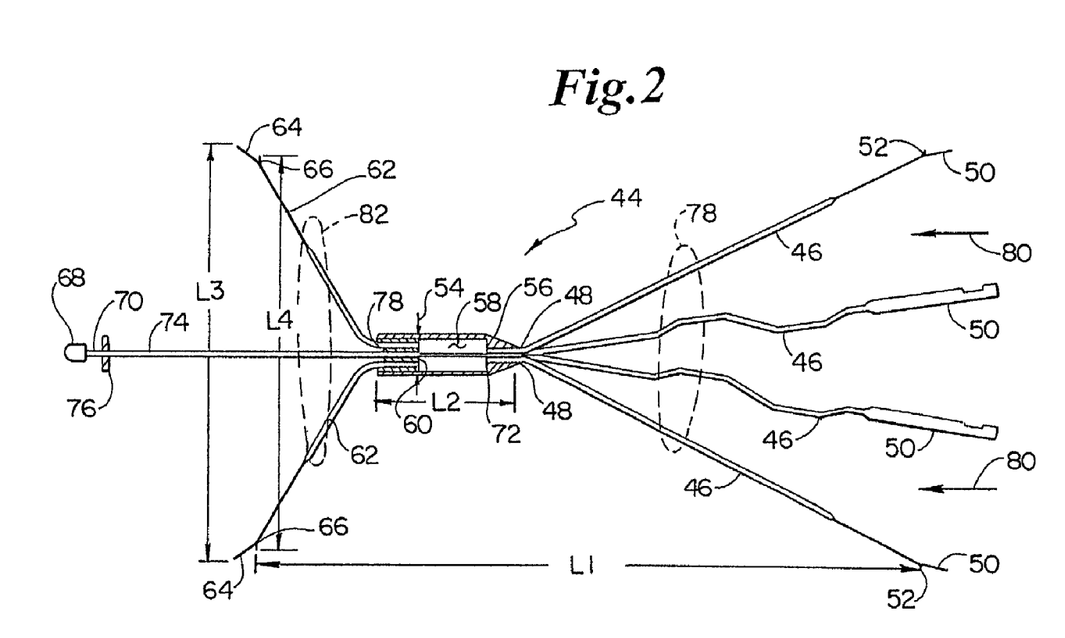
FIG. 2 is a side cutaway view of a filter in a relaxed position.

FIG. 2 is a side cutaway view of a filter in a relaxed position. The filter 44 has a plurality of shaped filtering elements 46, each having a mounting end 48 and a wall engaging end 50. Projections 52 have a length sufficient to engage an associated vein wall (not shown) while being short enough so the vein will not be pierced.

Connecting structure 54 has a frustum shaped end 56 that fixedly attaches the mounting ends 48. Structure 54 defines a longitudinal cavity 58 within which mounting member 60 is slidably retained.

A plurality of flexible anchoring struts 62 are mounted on mounting member 60 and project outwardly to wall engaging surfaces 64. Projections 66 function to position and hold the filter 44 in position when engaged to an inner vein wall. A hooking element 68 is affixed to mandrel 70. An end 72 of mandrel 70 is affixed within the connecting structure 56. A tubular member 74 has one end affixed to a pushing structure 76 and a second end 78 mounted in the mounting member 60. Tubing 74 surrounds a mandrel 70 and is coaxially aligned therewith.

In the relaxed state, the length L1 from projection 52 to projection 66 is in the order of 2.0 inches. The length L2 of the joining member 54 is about 0.4 inch. The tip-to-tip length L3 is in the order of 1.25 inches, and the projection-to-projection distance L4 is in the order of 1.2 inches. Various configurations and geometries will be described below, it being understood that when deployed, the filtering portion shown at dashed line 78 will function to restrict the flow of blood clots or thrombosis when blood is flowing in the direction of arrows 80. At the same time, positioning and holding portion 82 will restrict longitudinal and transverse movement of the filter 44 within the associated lumen or vein. Holding portion 82 preferably centers the device within the lumen.

Figure 3:
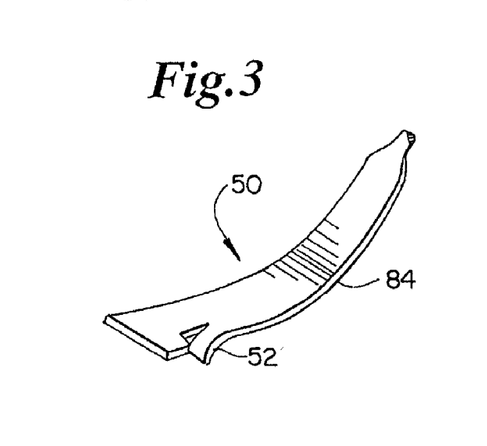
FIG. 3 is a partial perspective view of the vein engaging end of a filter leg member.

FIG. 3 is a partial perspective view of the vein engaging end of a filter leg member. The end member 50 has a generally curved structure and is flattened to a desired dimension such that the under surface 84 will slidably engage an associated vein wall. The thickness is selected for the desired flexibility. An outward projection 52 is arranged for engaging the vein wall. A similar configuration is utilized for the anchoring elements.

Figure 4:
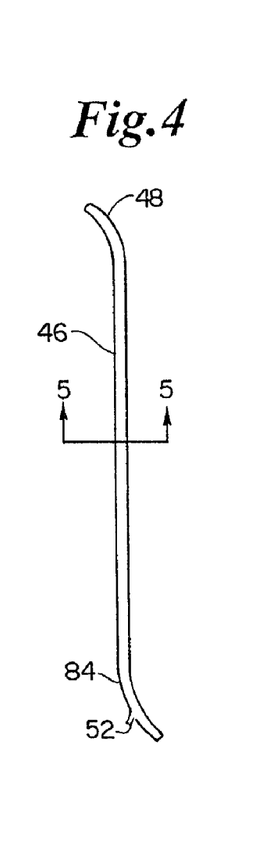
FIG. 4 is a side view of a ribbon wire leg member.

FIG. 4 is a side view of a ribbon wire leg member. The filter member 46 has the mounting end 48 positioned at a predetermined angle to the longitudinal arrangement of the member 46. At its other end, the curved portion 84 deflects in the opposite direction and has projection 52.

Figure 5:
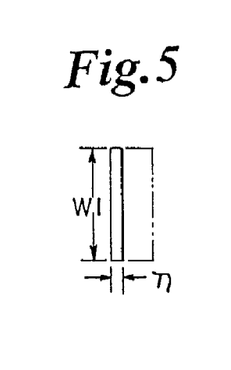
FIG. 5 is a cross-sectional view taken at line 5-5 in FIG. 4.

FIG. 5 is a cross-sectional view taken at line 5-5 in FIG. 4. In one configuration, the flat wire has a thickness T1 of about 0.006 inch and a width W1 of about 0.026 inch. It is, of course, understood that differences in thickness relative to width will effect the flexibility of the element.

Figure 6:
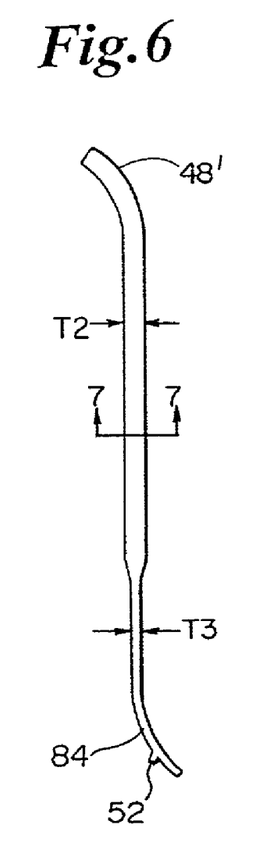
FIG. 6 is a side view of a round leg member.

FIG. 6 is a side view of a round leg member. Again, the leg member has a deflection 48' and has an upper thickness T2 that can be in the order of 0.016 inch. The lower portion has a reduced cross section with a thickness T3 in the order of about 0.006 inch.

Figures 7, 8:
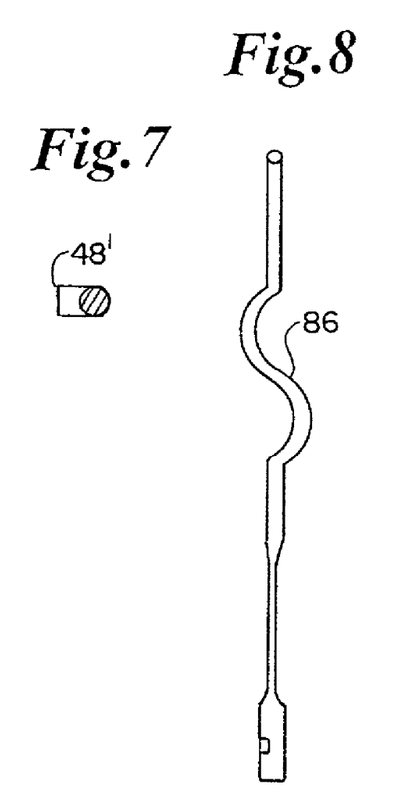
FIG. 7 is a cross-sectional view taken at line 7-7 in FIG. 6.
FIG. 8 is a plan view of a serpentine shaped leg member.

FIG. 7 is a cross-sectional view taken at line 7-7 in FIG. 6. It illustrates the extent of deflection of portion 48'.

FIG. 8 is a plan view of a serpentine shaped leg member. As illustrated, serpentine section 86 is provided to yield an improved filtering function when used in combination with other filter members.

Figure 9:
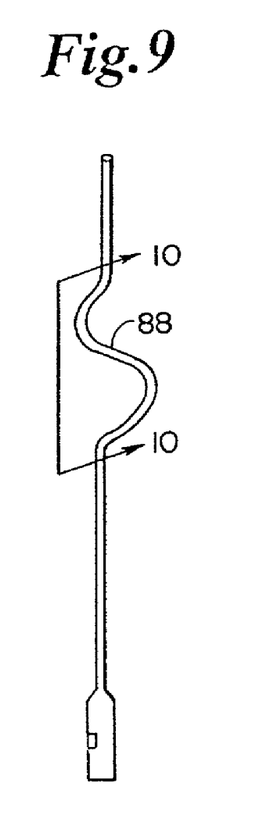
FIG. 9 is a plan view of a spiral shaped leg member.

FIG. 9 is a plan view of a spiral shaped leg member. In this alternative embodiment, a spiral portion 88 is utilized to enhance the filtering operation.

Figure 10:
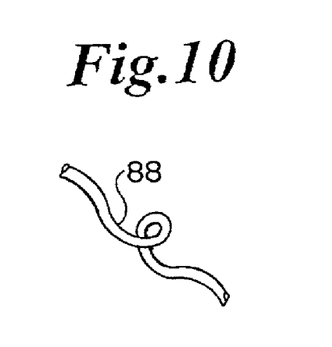
FIG. 10 is a partial perspective view taken at line 10-10 in FIG. 9.

FIG. 10 is a partial perspective view taken at line 10-10 in FIG. 9. It illustrates the spiral portion 88. The design of serpentine portion 86 or spiral portion 88 will be selected in accordance with the number of the filter elements used, the overall size of the filter 44, the attributes of the lumen in which it will be installed, and the flow of blood being filtered.

Figure 11:
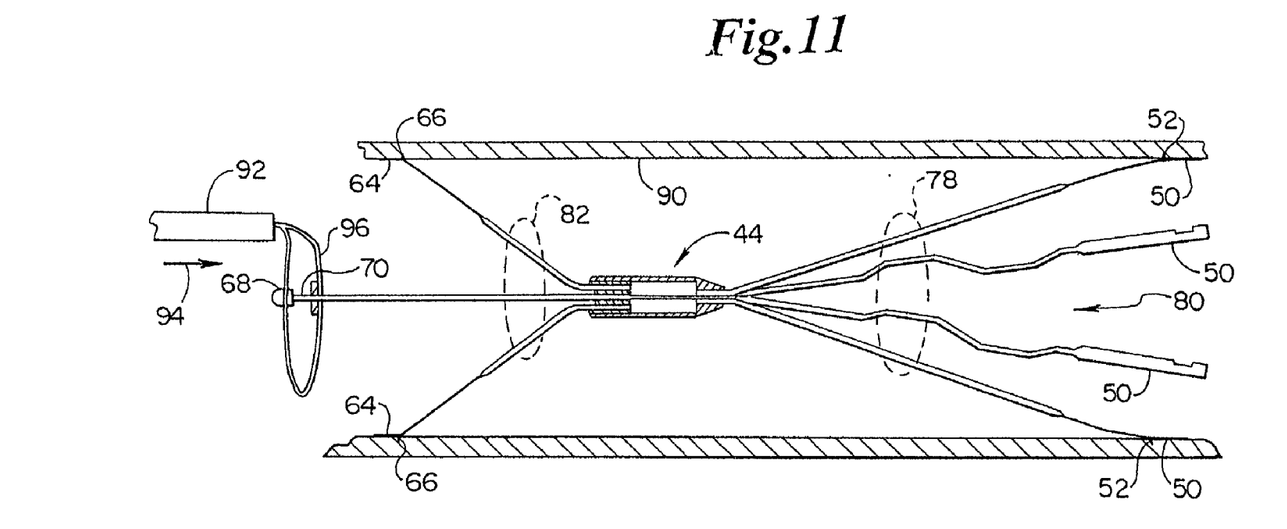
FIG. 11 is a side cutaway view of a filter positioned in a lumen about to be engaged for removal.

FIG. 11 is a side cutaway view of a filter positioned in a lumen about to be engaged for removal. It will be noted that the positioning portion 82 and the filtering portion 78 have their respective members deflected within the confines of vein 90. As deflected, the curved engaging portions 50 are brought in contact with the inner wall 90, as are contact portions 64 of the positioning portion 82. This arrangement provides for the vein walls 90 to provide adequate tension on the positioning portion 82 and the filtering portion 78 to cause the projections 52 and 66 to engage the inner wall without piercing the inner wall.

A filter recovery mechanism 92 is inserted in the direction of arrow 94 until a grasping mechanism 96 is brought in proximity to hooking element 68. Snare 96 is a looped cord or wire that can be externally manipulated to engage mandrel 70 behind the hooking element 68. In one configuration, the hooking element 68 and the grasping mechanism 96 can be constructed of materials that can be tracked fluoroscopically.

Figure 12:
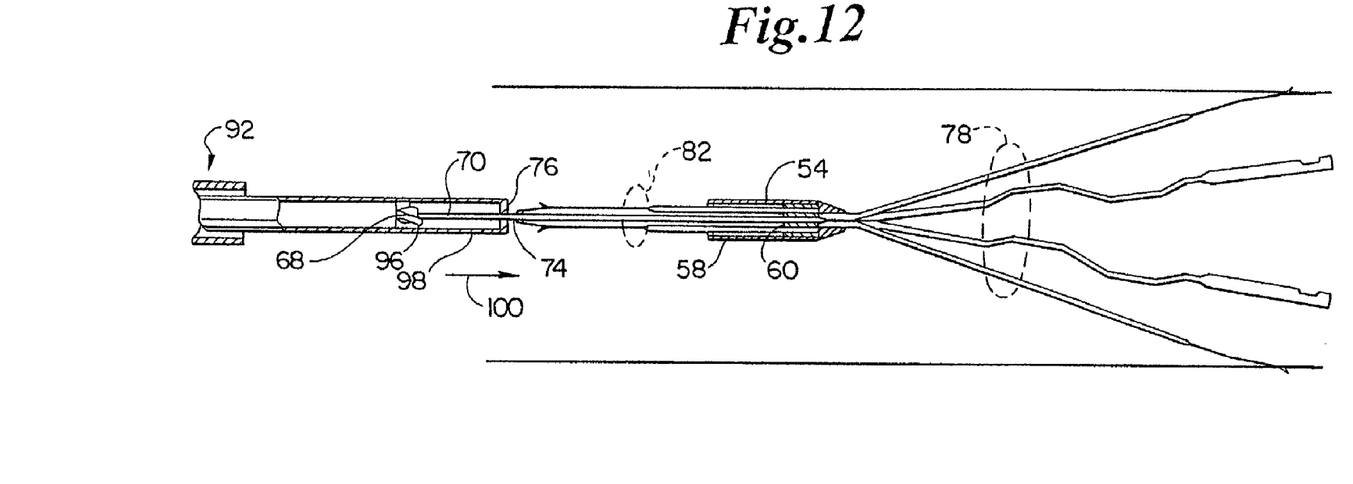
FIG. 12 is a side cutaway view of a filter positioned in a lumen having a positioning portion collapsed for removal.

FIG. 12 is a side cutaway view of a filter positioned in a lumen having the positioning portion collapsed for removal. When the extensible gripping device 96 engages members 68, it can be utilized to hold member 68 in a relatively fixed longitudinal position. When thus arranged, actuating device 98 is moved in the direction of arrow 100 to engage element 76 to thereby force tube 74 to move along mandrel 70 and cause the positioning portion 82 to collapse. Mounting element 60 is moved within cavity 58 to effect the collapse, and cause the positioning elements to be substantially parallel aligned along the longitudinal axis.

Figure 13:
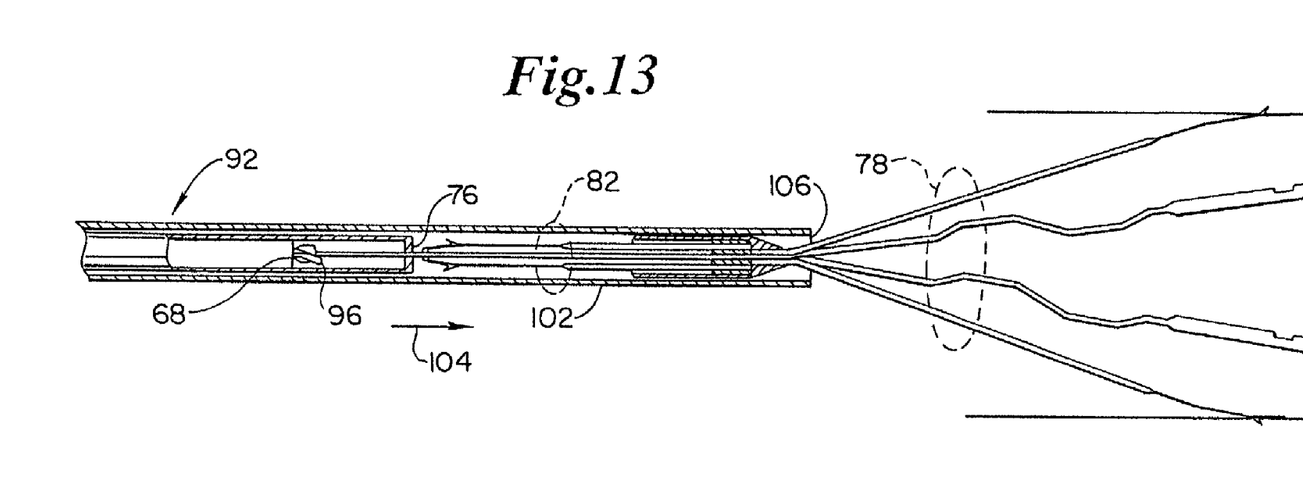
FIG. 13 is a side cutaway view of a filter positioned in a lumen having the positioning portion enclosed within a recovery mechanism.

FIG. 13 is a side cutaway view of a filter positioned in a lumen having the positioning portion enclosed within a recovery mechanism. Once the positioning portion 82 has been collapsed, outer shield 102 is moved in the direction of arrow 104 while the gripping device is held steady. When thus positioned, the outer shield 102 is positioned at end 106 to engage the filtering elements 78.

Figure 14:
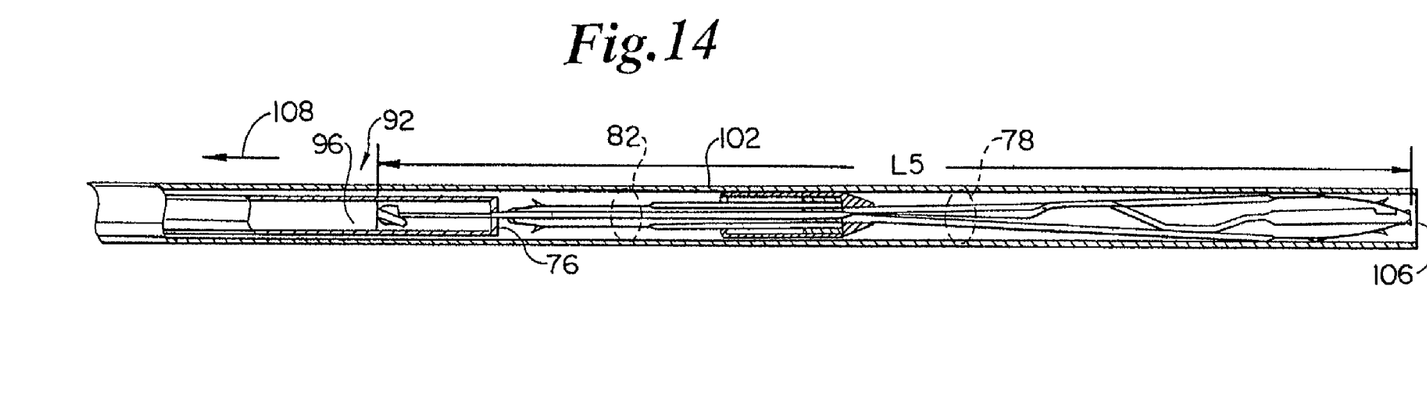
FIG. 14 is a side cutaway view of a filter positioned within a lumen having the entire filter enclosed within a recovery mechanism and ready for removal.

FIG. 14 is a side cutaway view of a filter positioned within a lumen having the entire filter enclosed within a recovery mechanism and ready for removal. Once the positioning portion 82 is enclosed within outer shield 102, pressure can be applied to the gripping member 96 for moving the gripping member in the direction of arrow 108. When thus moved, the outer shield 102 is held firm and end 106 functions to collapse filtering portion 78 such that it can be withdrawn within the confines of outer shield 102. When fully withdrawn within the recovery mechanism 92, the relatively stiff portion of the recovery mechanism 92 has a length L5 of about 2.77 inches.

Figure 15:
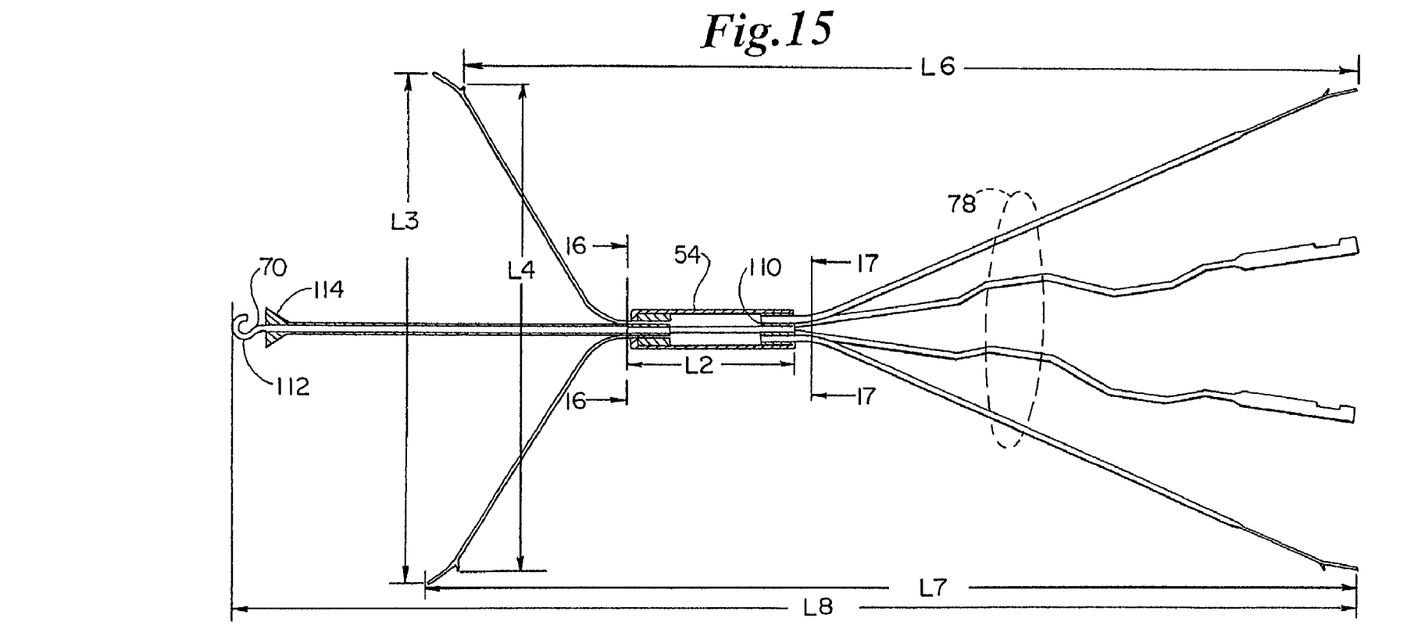
FIG. 15 is a side cutaway view of another embodiment of a filter in a relaxed position.

FIG. 15 is a side cutaway view of another embodiment of a filter in a relaxed position. Elements having similar functions will have a similar reference numeral designation. In this embodiment, filtering portion 78 is mounted in mounting structure 110 enjoining member 54. This configuration eliminates the frustum element 56 and provides additional strength at this structure. A hook 112 replaces the button element 68. Pushing element 76 of FIG. 2 is replaced by a pushing frustum element 114. This frustum configuration provides an improved blood flow and minimizes turbulence. Further, it gives a larger dimension along mandrel 70 such that there is minimization of the tendency to tilt as it is being moved forward as previously described. In this embodiment, dimensions L2, L3, and L4 are similar to those described with regard to FIG. 2. The projection-to-projection length L6 is in the order of 2.1 inches, while the tip-to-tip length L7 is in the order of about 2.22 inches. Finally, the over-all relaxed length of the filter is designated L8, and is about 2.68 inches.

Figure 16:
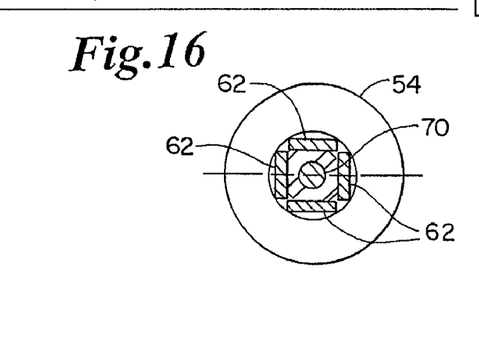
FIG. 16 is an end view of a joining member taken at line 16-16 in FIG. 15.

FIG. 16 is an end view of a joining member taken at line 16-16 in FIG. 15. It illustrates the housing 54 mounting positioning elements 62, which number four in this configuration, surrounding mandrel 70 which passes therethrough. This figure is expanded and is not in scale.

Figure 17:
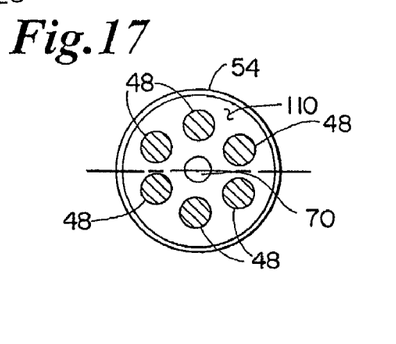
FIG. 17 is an end view of a joining member taken at line 17-17 in FIG. 15.

FIG. 17 is an end view of a joining member taken at line 17-17 in FIG. 15. It illustrates the mounting member 110 which is mounted in the connecting housing 54, and shows six mounting ends 48 of the filtering members. Mandrel 70 is affixed in the mounting member 110. Again, this figure is in a different scale to that of FIG. 15.

Figure 18:
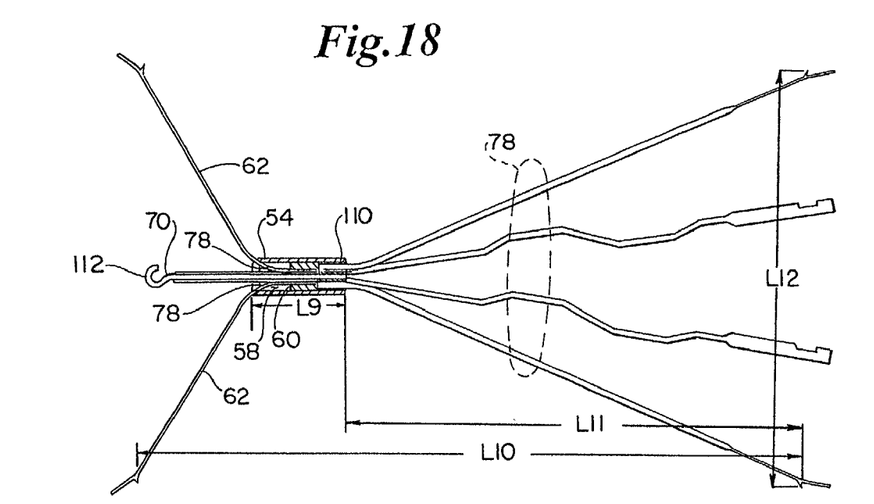
FIG. 18 is a side cutaway view of yet another embodiment of a filter in a relaxed position.

FIG. 18 is a side cutaway view of yet another embodiment of a filter in a relaxed position. In this embodiment, the mounting element 60 is fixedly mounted within channel 58 substantially adjacent to mounting member 110. The mounting ends 78 of positioning struts 62 are restrained by the outer limits of housing 54. A hook 112 is fixedly mounted to mandrel 70 which in turn is secured in mounting element 110. In this embodiment, housing 54 is shorter than the embodiment illustrated in FIG. 2, and has a length L9 of about 0.265 inch. The overall length L10 from a projection-to-projection is in the order of 1.85 inches, and the length L11 from the end of mounting member 110 to the filtering portion 78 projections is in the order of 1.27 inches. The relaxed spacing of the filtering portion L12 is in the order of 1.2 inches. The releasing and collapsing of the anchoring elements 62 in this embodiment will be described below.

Figure 19:
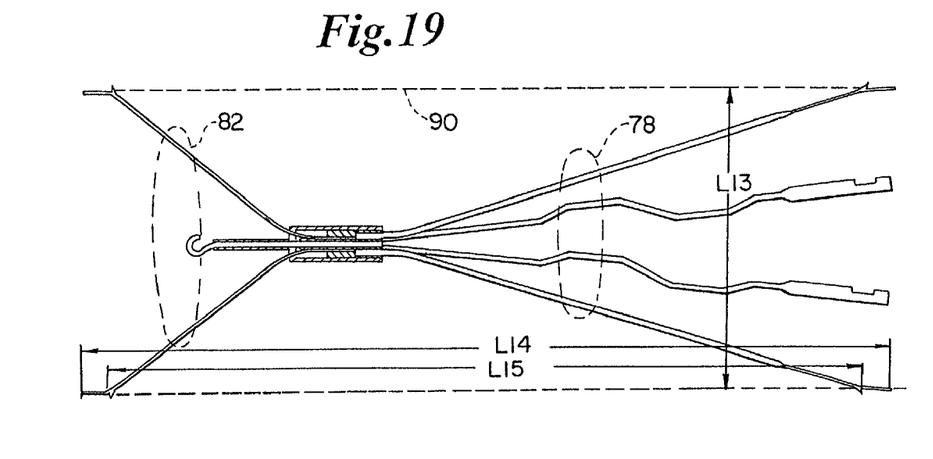
FIG. 19 is a side cutaway of the filter of FIG. 18 positioned in a lumen.

FIG. 19 is a side cutaway of the filter of FIG. 18 positioned in a lumen. As shown, positioning portion 82 engages the inner vein wall 90, as does the filtering portion 78. When thus contained, the diameter of the lumen or vein L13 is in the order of 0.866 inch. When installed, the overall length L14 is in the order of 2.25 inches, while the tip projection-to-projection length L15 is in the order of 2.11 inches.

Figure 20:
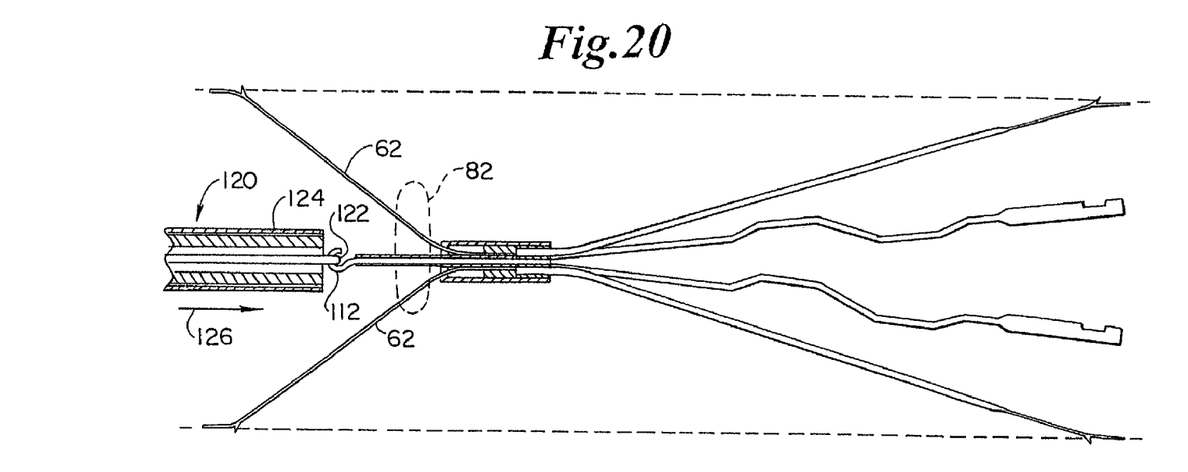
FIG. 20 is a side cutaway of the filter of FIG. 18 engaged for removal.

FIG. 20 is a side cutaway of the filter of FIG. 18 engaged for removal. In this embodiment, a recovery mechanism 120 has a gripping device 122 for engaging hook 112. When thus engaged, the gripping device can be held firmly externally, and the outer shield 124 extended in the direction of arrow 126 to engage the legs 62 of positioning portion 82. Outer shield 24 can include a funnel shaped end to assist in directing the filter into the recovery mechanism 120.

Figure 21:
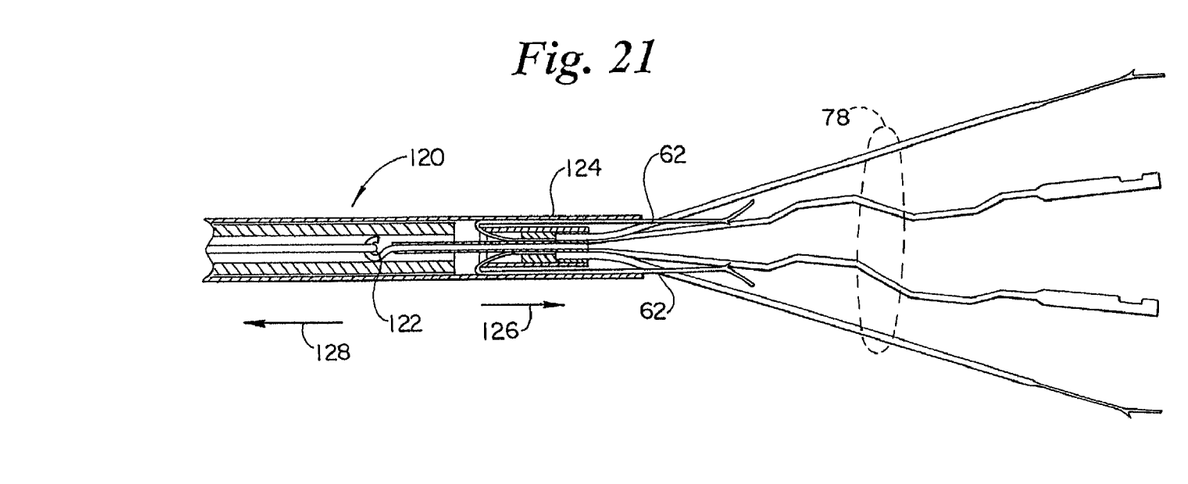
FIG. 21 is a side cutaway of the filter of FIG. 18 with the positioning portion enclosed within a recovery mechanism.

FIG. 21 is a side cutaway of the filter of FIG. 18 with the positioning portion enclosed within a recovery mechanism. As shown, the recovery mechanism 120 has had the outer shield 124 moved farther in the direction of arrow 126 such that positioning struts 62 have been bent back upon themselves and are within outer shield 124. As thus positioned, struts 62 are substantially parallel to each other and aligned along the longitudinal axis of the filter and the recovery mechanism 120. When the positioning portion is thus collapsed and retracted, the outer shield 124 is held stationary and the gripping device 122 is moved in the direction of arrow 128 for drawing the filtering portion 78 into outer shield 124. When the filtering portion 78 is fully withdrawn within outer shield 124, the recovery mechanism 120 can be withdrawn from the body.

Figure 22A:
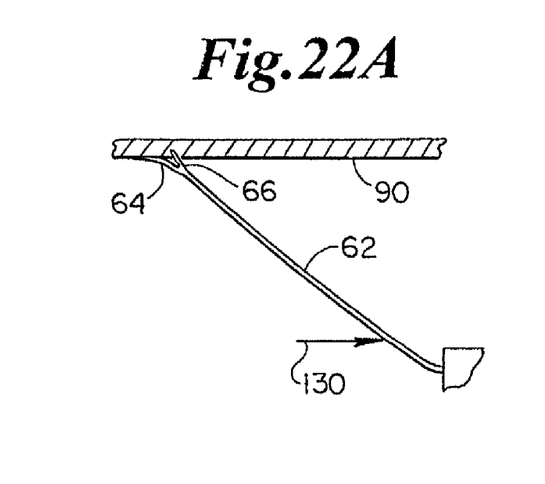
FIGS. 22A-22E illustrate the deflection and retraction of a flexible anchor member of the type used with the filter of FIG. 18.
Figure 22B:
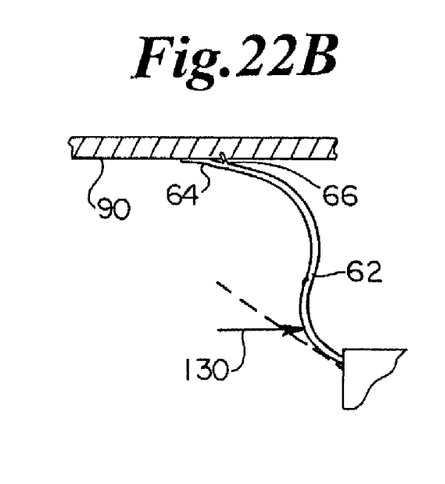

FIGS. 22A-22E illustrate the deflection and retraction of a flexible anchor member of the type used with the filter of FIG. 18. In FIG. 22A, a flexible anchor member 62 is in a holding position on the inner wall of vein 90. As force is applied in the direction of arrow 130 to the portion of flexible anchor member 62 by the outer shield 124 (see, FIG. 21), the tip 64 and the protrusion 66 are started in a direction to be released from the inner wall 90. In FIG. 22B, the force has been applied at arrow 130 to start deflection of flexible anchor member 62. At this juncture, the protrusion 66 has been removed from inner wall 90 and the tip 64 has started to slide along the inner wall. Anchor member 62 can have a predetermined region of greater flexibility to control the location of the deflection caused by the force supplied at arrow 130.

Figure 22C:
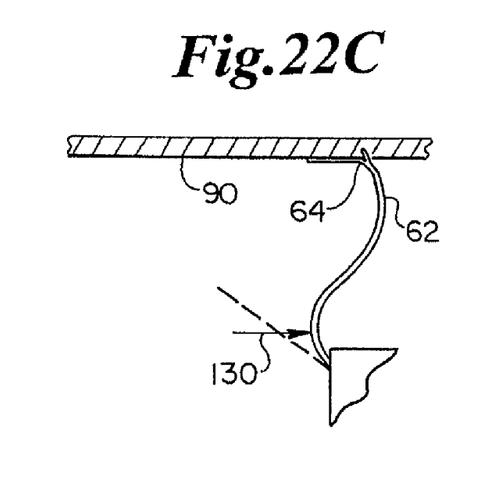
Figure 22D:
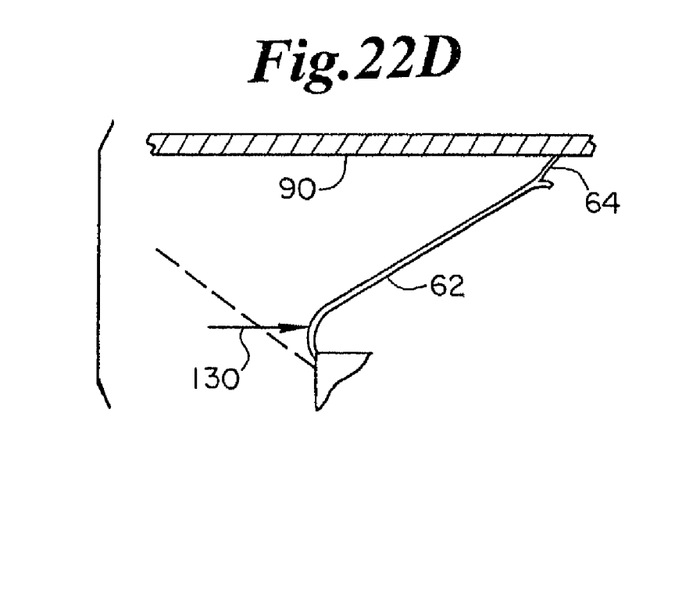
Figure 22E:
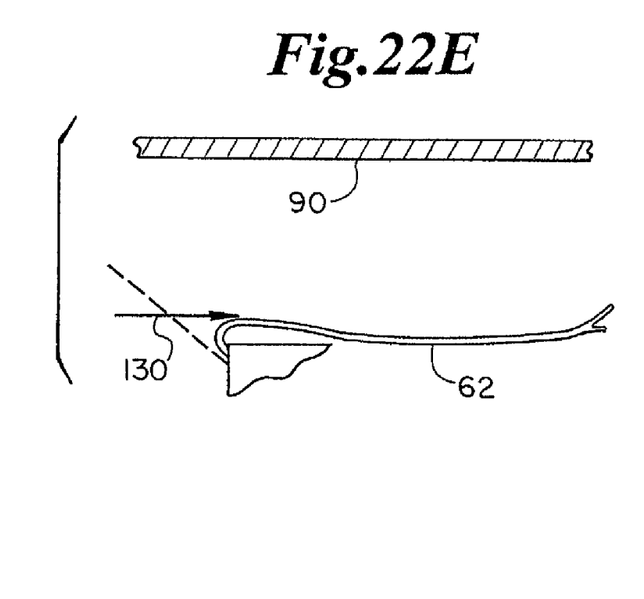

In FIG. 22C, the force applied at arrow 130 has deflected flexible anchor member 62 such that the end 64 is merely moving along the inner wall surface 90. In FIG. 22D, there is an illustration that the force applied in the direction of arrow 130 has proceeded to a point where flexible anchor member 62 has started to bend back upon itself, and the tip 64 is out of contact with the inner wall of vein 90. Finally, in FIG. 22E, it is shown that force applied in the direction of arrow 130 by the outer shield 124 as bent flexible anchor member 62 back upon itself, such that the outer shield can pass over it.

Figure 23:
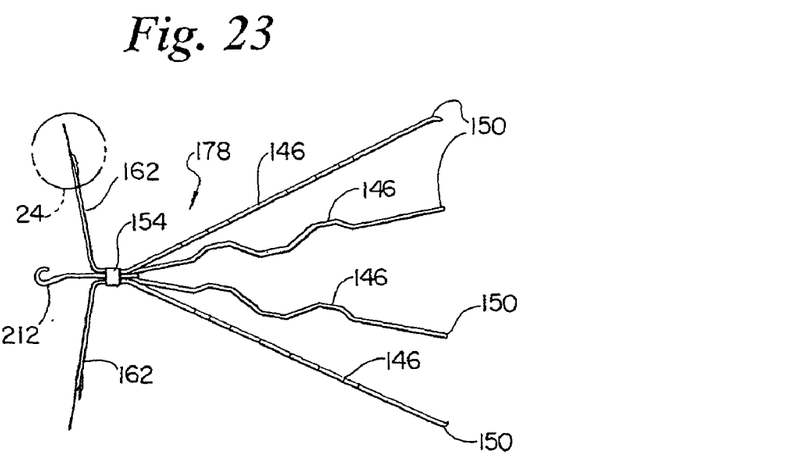
FIG. 23 is side view of yet another embodiment of the recoverable filter in accordance with the present invention.

FIG. 23 is a side view of yet another embodiment of a retrievable filter in accordance with the present invention. The filter as shown in FIG. 23 is in a relaxed, uncompressed state. The filter of FIG. 23 is substantially similar to that of FIGS. 15-22, except as the description below may vary from that of the embodiment of FIG. 15 described above.

Figure 24:
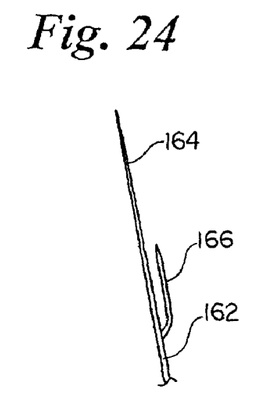
FIG. 24 is a detailed view of the distal end of an anchoring strut of the filter of FIG. 23.

The filter of FIG. 23 includes a plurality of filtering elements 146 having wall engaging ends 150. Wall engaging ends 150 as shown in this embodiment are curved to present a rounded convex face to a vessel wall. Collectively filtering elements 146 form a filter portion or array 178. Disposed distally of filter array 178 are a plurality of legs or anchoring struts 162. Anchoring struts 162 have proximal and distal ends. A typical distal end is shown in FIG. 24 in detail. The filter also includes a hook 212 to aid in removal of the filter from a vessel. An enjoining member 154 joins filter array 178, struts 162 proximate their proximal ends and hook 212 together. Struts 162 preferably are formed in a ribbon shape, wherein the thickness of the ribbon is shown in FIG. 23 and the width is perpendicular to the thickness, i.e., directly into the paper.

FIG. 24 is a detailed view of the distal end of a strut 162. The distal end includes a sharpened portion 166 and a pad portion 164 extending distally beyond sharpened portion 164. Sharpened portion 164 is sufficiently sharp to penetrate a vessel wall. Pad portion 164 similarly to strut 162, preferably has a ribbon shape wherein the thickness is shown in FIG. 24 and the width is perpendicular to the thickness, i.e., directly into the paper. As can be seen in FIG. 24, the thickness of pad portion 164 decreases distally. The decrease in pad thickness 164 can create an increase in flexibility of pad portion 164 distally. A similar increase in flexibility distally along pad portion 164 can be created by varying the material characteristics of pad 164. Pad portion 164 is preferably flexible enough not to puncture the vessel wall, i.e., the pad portion 164 is preferably atraumatic. In a preferred embodiment of the present invention, the length of sharp portion 164 is between about 2 to 6 millimeters and the length of pad portion 162 is between about 4 to 20 millimeters. In a preferred embodiment, pad portion 164 is more than twice as long as sharp portion 164.

Figures 25, 26, 27, 28:
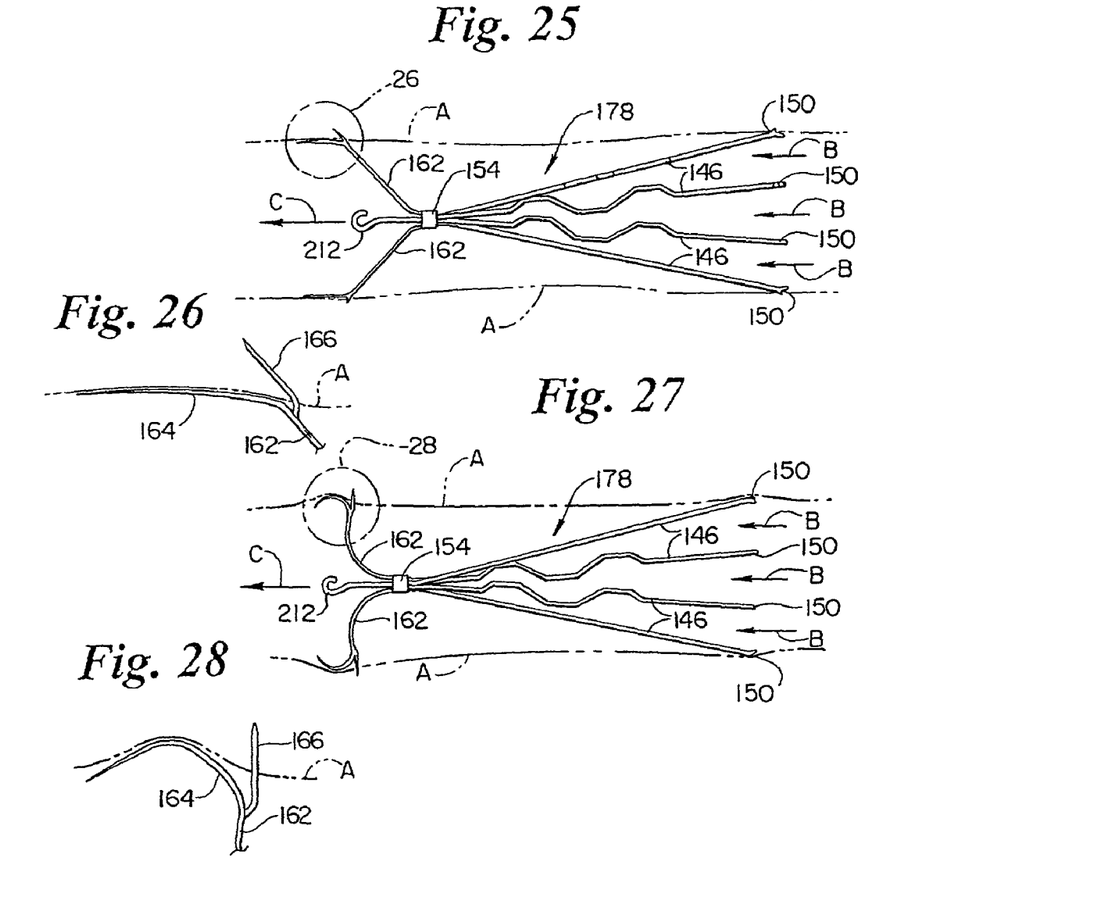
FIG. 25 is a side view of the recoverable filter of FIG. 23 disposed in a vessel lumen.
FIG. 26 is a detailed view of the distal end of an anchoring strut as shown in FIG. 25.
FIG. 27 is a side view of a recoverable filter of FIG. 23 shown in a vessel lumen during the process of removing the filter from the vessel lumen.
FIG. 28 is a detailed view of the distal end of an anchoring strut shown in FIG. 27.

FIGS. 25 and 26 show the filter of FIG. 23 disposed in a vessel A during normal use. The direction of blood flow is shown by arrows B. The removal of the filter would be in the direction indicated by arrow C by way of hook 212. Filter elements 146 are shown moderately compressed in comparison to their relaxed state shown in FIG. 23. As shown in FIG. 26, sharp portion 166 is penetrating the wall of the vessel A and pad portion 164 is generally parallel to the wall of vessel A.

FIGS. 27 and 28 show the filter of FIG. 23 in the process of being removed from vessel A in the direction indicated by arrow C. As the filter is withdrawn using the same procedure as that of the filter of FIG. 15, struts 162 will deform generally as shown in FIGS. 22A-22E. Strut 162 as shown in FIG. 27 is in the approximate position of strut 62 in FIG. 22B. As the process continues, strut 162 will assume generally the position shown in FIG. 22E. The ultimate removal of the filter will be accomplished as described with respect to the filter of FIG. 15 above.

FIG. 28 is a detailed view of the distal end of strut 162 as shown in FIG. 27. Although the configuration of strut 162 in FIG. 27 is similar to that of strut 62 in FIG. 22B, it can be appreciated that the length of pad portion 164 relative to sharpened portion 166 is substantially greater than element 64 is to element 66 of FIG. 22B, respectively. As can be appreciated the increased length and increasing flexibility of pad portion 164 distally provides an effective cantilever for retracting sharp portion 166 from the wall of vessel A.

Figures 29, 30, 31:
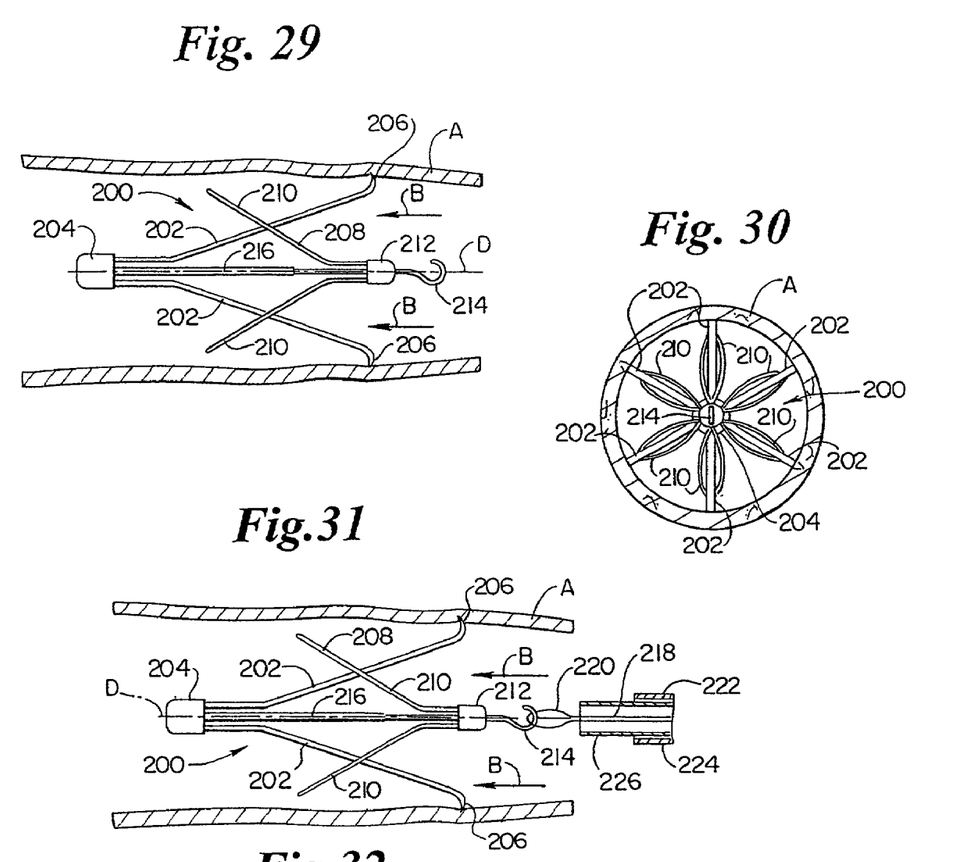
FIG. 29 is a side view of yet another embodiment of a recoverable filter in accordance with the present invention.
FIG. 30 is an end view of the filter of FIG. 29.
FIG. 31 is a view of the filter of FIG. 29 and a removal catheter.

FIG. 29 is a side view of yet another embodiment of filter 200 in accordance with the present invention disposed within a vessel A. Filter 200 has a longitudinal axis D. Blood or fluid flow in vessel A is shown in the direction indicated by arrows B. Filter 200 includes flexible struts 202 generally extending in the first direction along axis D from a hub 204, while diverging from axis D. A first end of strut 202 is coupled to hub 204. Second end 206 of strut 202 is preferably sharpened and barbed to engage with the wall of vessel A.

Filter 200 also includes a strut retraction member 208. Strut retraction member 208 includes a plurality of retraction loops 210 extending from retraction member hub 212 generally in the second direction along axis D. Each of loops 210 preferably loops around a strut 202. A tether connector 214 extends from hub 212 in the first direction along axis D. A telescoping connector 216 connects hub 204 and retraction member hub 212.

Various elements of filter 200 such as struts 202 or loops 210 may be formed from nitinol, stainless steel or other biocompatible materials. One skilled in the art would appreciate that the materials described above with respect to the other filter embodiments could advantageously be applied to construct the embodiment 200 as well.

FIG. 30 is an end view of filter 200 shown within vessel A. In the illustrated embodiment of filter 200 there are six struts 202 and loops 210.

FIG. 31 is a side view of the filter of FIG. 29 to which a tether 218 having a loop 220 is attached to tether connector 214. Tether 218 is disposed within a catheter 222 having an outer tubular member 224 and an inner tubular member 226. Assuming that, for example, filter 220 is disposed in the inferior vena cava, catheter 222 may be advanced to the filter from a femoral vein access point. Outer tube 224 and inner tube 226 are preferably formed from biocompatible materials including polymers known to those skilled in the art. The materials must be of sufficient strength and rigidity or flexibility to accomplish the procedure described below.

Figure 32:
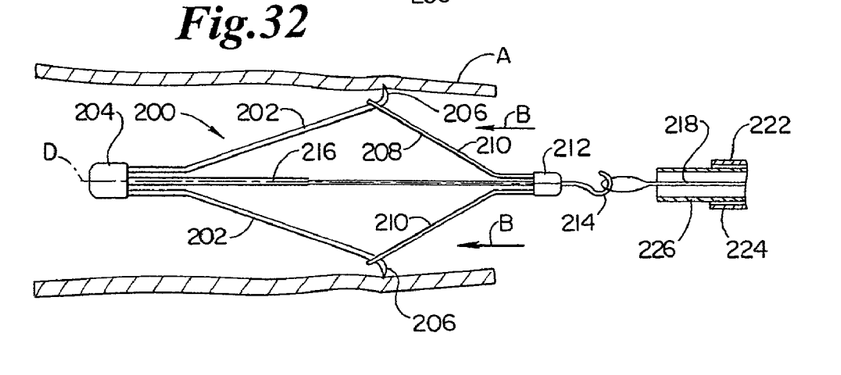
FIG. 32 is a view of the filter of FIG. 29 in an early stage of the removal process.
Figure 33:
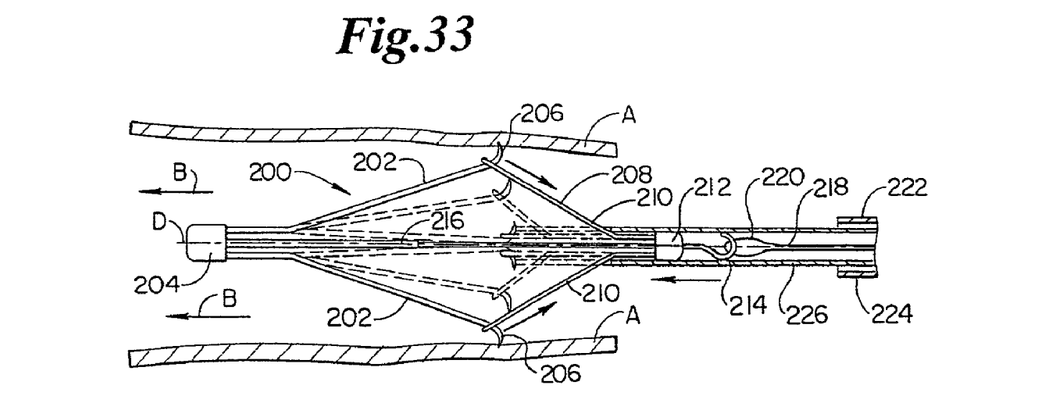
FIG. 33 is a view of the filter of FIG. 29 in a stage of the removal process subsequent to that shown in FIG. 32.

FIG. 32 is a side view of the filter of FIG. 29 wherein the retraction member 208 is being pulled in the first direction such that loops 210 are advancing along and engaging struts 202. FIG. 33 is a side view of filter 200 of FIG. 29 wherein inner tube 226 of catheter 222 has been brought into engagement with loops 210. In dashed lines, inner tube 226 is shown being advanced in a second direction over loops 210 such that struts 202 are brought from a first position engaging the walls of vessel A to a second position adjacent axis D of filter 200.

Figure 34:
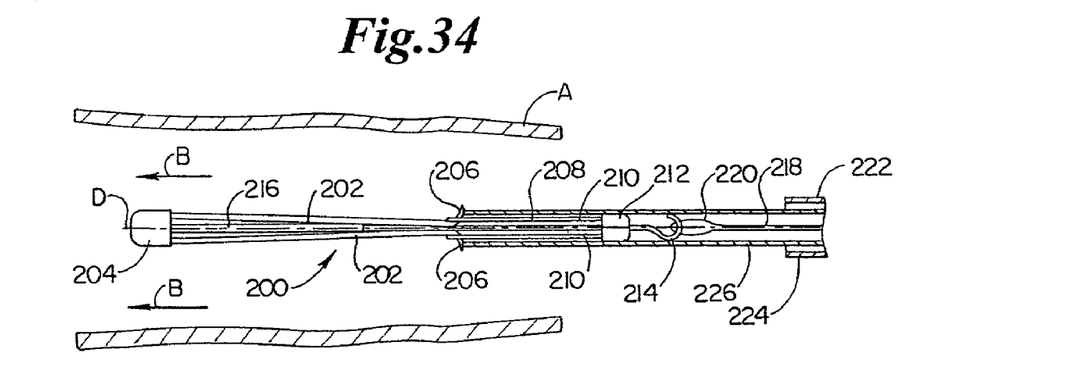
FIG. 34 is a view of the filter of FIG. 29 in a stage of the removal process subsequent to that shown in FIG. 33.

FIG. 34 is a side view of filter 200 shown in FIG. 29. In FIG. 34 struts 202 are shown disposed in the second position. Second ends 206 of struts 202 have been brought into contact with the distal end of inner tube 226.

Figure 35:
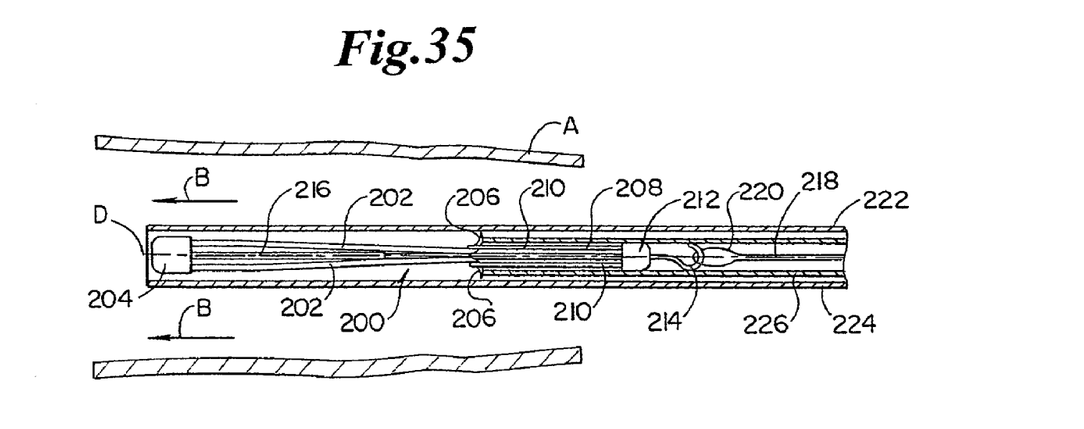
FIG. 35 is a view of the filter of FIG. 29 shown withdrawn into the removal catheter.

FIG. 35 is a side view of filter 200 of FIG. 29 in which filter 200 has been withdrawn into outer tube 224 of catheter 222. Filter 200 could now be removed from the patient through outer tube 224, or filter 200 and catheter 222 could be simultaneously removed from the patient.

It can be appreciated that performing the steps of removal process in reverse would provide a method of placing filter 200 in vessel A as shown in FIG. 29. In a preferred method, however, hubs 204 and 212 would be spaced as shown in FIG. 29 prior to placement in catheter 222. After deployment of filter 200, as shown in FIG. 29, tether 218 and catheter 222 can be removed from the patient such that filter 200 may remain in place for an extended period of time.

From the foregoing, it is understood that various configurations and selection of materials will provide suitable removable filter structures that may be utilized in conformance with the inventive concepts described herein. In general, it is understood that the materials must be suitable for implantation in a human body and will remain intact without adding contaminants to the blood stream. The selection of materials will also determine the flexibility and resiliency of the various members. The various components of the filter can be constructed of a class of elastic materials including nitinol, stainless steel, platinum, tungsten, titanium, and chromium alloys. The shaping and bonding structures are those available in the construction of thrombosis filters of the class described.

Having described the various embodiments and methods of the invention in conjunction with the drawings, it can be seen that the various stated purposes and objectives have been achieved, and that various modifications and extensions will be apparent to those skilled in the art while remaining within the spirit and scope of the invention. Accordingly, what is intended to be protected by Letters Patent is set forth in the appended claims.

What is claimed is:

1. A retrievable intravascular filtering device having leading and trailing ends and a filter longitudinal axis, comprising:

a hub including a graspable member;

a plurality of elongate arms each having a joining portion joined to the hub, an engaging portion, and an arm longitudinal axis, said elongate arms being adapted and configured to shift between an expanded position and a collapsed position within a blood vessel, the arms being configured to extend outwardly away from the filter longitudinal axis in the expanded position; and anchoring means comprising a wall contacting portion for removably securing the intravascular filtering device to the blood vessel, said anchoring means having a first configuration in which at least a portion of the wall contacting portion is disposed in a direction generally parallel to the filter longitudinal axis and opposed to a direction from the hub toward the engaging portion of the plurality of elongate arms and a second configuration in which the wall contacting portion is disposed in a direction generally along the filter longitudinal axis in the direction from the hub toward the engaging portion of the plurality of elongate arms, said anchoring means being adapted to bend and deflect from the first configuration to the second configuration in response to a longitudinal force applied to the hub;

wherein said wall contacting portion includes a distal region of greater flexibility that is formed by a reduced cross-sectional area.

2. The filtering device of claim 1, wherein the anchoring means is adapted to bend within the region of reduced cross-sectional area while moving between the first configuration and the second configuration in response to a longitudinal force applied to the hub.

3. The filtering device of claim 1, wherein at least one of the elongate arms has a generally circular cross-section.

4. The filtering device of claim 1, wherein said plurality of elongate arms are filtering arms.

5. The filtering device of claim 1, wherein said anchoring means includes a flattened portion extending from the hub in the direction of the graspable member in the first configuration.

6. The filtering device of claim 1, wherein said anchoring means includes a sharpened portion.

7. The filtering device of claim 1, wherein said anchoring means includes a pointed hook.

8. The filtering device of claim 1, wherein said graspable member includes a hooking element.

9. The filtering device of claim 1, wherein said graspable member includes a pushing structure.

10. The filtering device of claim 1, wherein said graspable member includes a hooking element separated from a pushing structure by a mandrel.

11. A retrievable intravascular filtering device having leading and trailing ends and a filter longitudinal axis, comprising:

a hub including an axial graspable member extending toward the trailing end of the filter;

a plurality of elongate arms each having a joining portion joined to the hub, an arm longitudinal axis, and an engaging portion, said elongate arms being adapted and configured to shift between an expanded position and a collapsed position within a blood vessel, the arms being configured to extend outwardly away from the filter longitudinal axis in a direction towards the leading end of the filter in the expanded position; and anchoring means for removably securing the intravascular filtering device to the blood vessel, said anchoring means being adapted to bend and deflect from a trailing orientation to a leading orientation in response to a longitudinal force applied to the graspable member;

wherein said anchoring means includes a distal end having a greater flexibility that is formed by a reduced cross-sectional area.

12. The filtering device of claim 11, wherein the anchoring means is adapted to bend within the region of reduced cross-sectional area in response to a longitudinal force applied to the hub.

13. The filtering device of claim 11, wherein at least one of the elongate arms has a generally circular cross-section.

14. The filtering device of claim 11, wherein said plurality of elongate arms are filtering arms.

15. The filtering device of claim 11, wherein said anchoring means includes a flattened portion.

16. The filtering device of claim 11, wherein said anchoring means includes a sharpened portion.

17. The filtering device of claim 11, wherein said anchoring means includes a pointed hook.

18. The filtering device of claim 11, wherein said graspable member includes a hooking element.

19. The filtering device of claim 11, wherein said graspable member includes a pushing structure.

20. The filtering device of claim 11, wherein said graspable member includes a hooking element separated from a pushing structure by a mandrel.

21. A retrievable intravascular filtering device having leading and trailing ends and a filter longitudinal axis, comprising:

a hub including a graspable member;

a plurality of elongate arms each having a joining portion joined to the hub, an engaging portion, and an arm longitudinal axis, said elongate arms being adapted and configured to shift between an expanded position and a collapsed position within a blood vessel, the arms being configured to extend outwardly away from the filter longitudinal axis in the expanded position; and a plurality of pointed hooks for removably securing the intravascular filtering device to the blood vessel, said pointed hooks having a first configuration in which a wall contacting portion is disposed in a direction generally parallel to the filter longitudinal axis and opposed to a direction from the hub toward the engaging portion of the plurality of elongate arms and a second configuration in which the wall contacting portion is disposed in a direction generally along the filter longitudinal axis in the direction from the hub toward the engaging portion of the plurality of elongate arms, said pointed hooks being adapted to bend and deflect from the first configuration to the second configuration in response to a longitudinal force applied to the hub;

wherein said pointed hooks include a region of greater flexibility that is formed by a reduced cross-sectional area.

22. An intravascular thrombus filter having leading and trailing ends and a filter longitudinal axis, comprising:

a central hub disposed along the longitudinal axis, said hub including a graspable member;

a plurality of elongate arms each having a joining portion first end fixedly attached to the hub, and second end, the plurality of elongate members adapted to move between a contracted position and an expanded position, the plurality of elongate members forming a filter basket having an inlet opening at the second ends of the elongate members when in the expanded position; and a plurality of filter retaining members each having a sharp extremity for engagement with and penetration of the body vessel wall and a curved portion proximate the sharp extremity that is adapted to bend from a first position in which the filter retaining members are disposed in a first direction generally coinciding with that of the graspable member to a second position in which the plurality of filter retaining members are disposed in a second direction generally away from the hub and coinciding with the direction of the elongate members when a force is applied to the filter, facilitating removal of the sharp extremity from the body vessel wall without tearing the body vessel wall;

wherein said filter retaining members extend from an end of the hub adjacent to the graspable member;

wherein said sharp extremity includes a region of greater flexibility that is formed by a reduced cross-sectional area, wherein the plurality of filter retaining members is adapted to bend within the region of reduced cross-sectional area in response to a longitudinal force applied to the hub;

wherein the graspable member extends away from where the first end of each of the plurality of elongate members are fixedly attached to the hub.

* * * * *